(12) United States Patent
Quintin

(10) Patent No.: US 8,703,697 B2
(45) Date of Patent: Apr. 22, 2014

(54) METHOD FOR TREATING EARLY SEVERE DIFFUSE ACUTE RESPIRATORY DISTRESS SYNDROME

(76) Inventor: Luc Quintin, Villeurbanne (FR)

( * ) Notice: Subject to any disclaimer, the term of this patent is extended or adjusted under 35 U.S.C. 154(b) by 20 days.

(21) Appl. No.: 13/531,312

(22) Filed: Jun. 22, 2012

(65) Prior Publication Data

US 2012/0325209 A1     Dec. 27, 2012

Related U.S. Application Data

(60) Provisional application No. 61/500,720, filed on Jun. 24, 2011.

(51) Int. Cl.
*A61P 11/00*     (2006.01)

(52) U.S. Cl.
USPC ... 514/1.5; 514/211.13; 514/327; 128/204.18

(58) Field of Classification Search
USPC .................. 514/1.5, 211.13, 327; 128/204.18
See application file for complete search history.

(56) References Cited

U.S. PATENT DOCUMENTS

| | | | |
|---|---|---|---|
| 2010/0202979 A1* | 8/2010 | Horn | 424/45 |
| 2011/0142837 A1* | 6/2011 | Lambris et al. | 424/135.1 |

OTHER PUBLICATIONS

Chiumello et al., "Spontaneous breathing during mechanical ventilation," Crit. Care Med., 33(5):1170-1171 (2005).
Deans et al., "Mechanical ventilation in ARDS: One size does not fit all," Crit. Care Med., 33(5):1141-1143 (2005).
Dellinger et al., "Positive clinical impact of low tidal volume strategy," Crit. Care Med., 33(5):1143-1144 (2005).
Marini, "Spontaneously regulated vs. controlled ventilation of acute lung injury/acute respiratory distress syndrome," Curr. Opin. Crit. Care., 17:24-29 (2011).
Putensen et al., "Long-Term Effects of Spontaneous Breathing During Ventilatory Support in Patients with Acute Lung Injury," Am. J. Respir. Crit. Care Med., 164:43-49 (2001).
Shehabi et al., "Clinical application, the use of dexmedetomidine in intensive care sedation," Crit. Care & Shock, 13:40-50 (2010).
Voituron, et al., "Dexmedetomidine and clonidine induce long-lasting activation of the respiratory rhythm generator of neonatal mice: Possible implication for critical care," Respir. Physiol. Neurobiol., 180:132-140 (2012).
Wrigge et al., "Paralysis During Mechanical Ventilation in Acute Respiratory Distress Syndrome: Back to the Future?" Crit. Care Med., 32(7):1628-1630 (2004).

* cited by examiner

*Primary Examiner* — Savitha Rao
(74) *Attorney, Agent, or Firm* — McAndrews, Held & Malloy Ltd.

(57) ABSTRACT

A method for treatment of severe diffuse acute respiratory distress syndrome in an intubated-ventilated patient which includes sedating said patient with at least one alpha-2 agonist, maintaining spontaneous ventilation and applying pressure support ventilation of at least 5-10 cmH$_2$O combined to a high positive end expiratory pressure (PEEP) of 10-24 cmH$_2$O. A pharmaceutical composition containing at least one alpha-2 agonist suitable for treatment of ARDS in combination with, if appropriate, at least one sedative agent which does not depress ventilatory drive is also disclosed.

10 Claims, No Drawings

METHOD FOR TREATING EARLY SEVERE DIFFUSE ACUTE RESPIRATORY DISTRESS SYNDROME

RELATED APPLICATIONS

The present application claims the benefit of priority to U.S. Provisional Patent Application No. 61/500,720, which was filed on Jun. 24, 2011. The entire text of the aforementioned application is incorporated herein by reference in its entirety.

FEDERALLY SPONSORED RESEARCH OR DEVELOPMENT

[Not Applicable]

FIELD OF THE INVENTION

The present invention relates to treatment of early severe acute respiratory distress syndrome (ARDS).

BACKGROUND OF THE INVENTION

ARDS is a syndrome in which closed alveoli do not perform oxygenation while blood flow still perfuse the capillaries surrounding the closed alveoli. This leads to a low ventilation/perfusion ratio (VA/Q) and severe hypoxia. However, upon early ARDS, there is no respiratory pump failure: the disease is restricted to oxygenation not to elimination of CO2.

Patients diagnosed with acute respiratory distress syndrome ("ARDS"), are typically treated with controlled mechanical ventilation (CMV) and conventional sedation (typically benzodiazepine-opiate: usually midazolam-sufentanil) and, optionally, a muscle relaxant. Upon refractory hypoxia, adjunctive therapy may be required: prone positioning, NO, sildenafil, almitrine, etc. . . . . Most patients do not die from refractory hypoxia but from pre-existing co-morbidities or complications arising from prolonged stay in the critical care unit (CCU): sepsis, cardiac failure, multiple organ failure (MOF). Therefore, contrary to the views expressed by authorities (1), treatment of ARDS is to shorten the length of intubation (i.e. "fast-tracking" extubation), stay in the CCU and reduce the incidence of iatrogenic complications.

The core progress over the last 10 years was the combination of a few physiological and epidemiological studies, to avoid barotrauma and volutrauma: a) use of a Pplat (maximal pressure measured upon end-inspiration)≤26-32 cm H2O b) use of low tidal volumeVt≤5-6 ml·kg-1 of body weight (BW) compatible with such a low Pplat. However, the cornerstone of the treatment still relies on CMV (or related modes of ventilation: assist control, IMV, etc.) at variance with maintenance of spontaneous ventilation. Worse, some advocate the use of an early 48 h course of myorelaxation (2). Most commentators have skipped the fact that this group switches his patients over to spontaneous ventilation-pressure support (SV-PS) after this 48 h course (2, 3).

Few groups advocate the use of spontaneous ventilation (SV) upon ARDS (4-6), without a clear-cut schema for this use. Moreover, experienced investigators advocate against the use of SV upon early severe ARDS, when oxygen demands are high (7). The only group which provides such a clear-cut schema, uses a combination of midazolam and opiates which a) depresses the ventilator drive, at variance with the use of SV b) generates an elimination process which appears at odd with the objective of fast tracking the extubation. The article which describes this known method is: "Putensen C, Zech S, Wrigge H, Zinserling J, Stuber F, von S T, et al. *Long-term effects of spontaneous breathing during ventilatory support in patients with acute lung injury. Am J Respir Crit Care Med.* 2001; 164(1): 43-9" (5).

BRIEF SUMMARY OF THE INVENTION

The present invention is directed to a method for treating a patient suffering from acute respiratory distress syndrome (ARDS) via the combination of
  a) administering to the patient of at least one alpha-2 agonist as first-line sedative agent
  b) subjecting the patient to any ventilator mode, which will respect spontaneous ventilation: pressure support, etc.

According to one embodiment of the invention, a method is provided for treating an intubated-ventilated ARDS patient, said method comprising the following steps:
  a) sedating said patient with a sedating agent S comprising at least one alpha-2 agonist,
  b) applying high positive end expiratory pressure PEEP: 10-24 cm H2O;
  c) maintaining spontaneous ventilation and applying pressure support ventilation: 5-10 cm $H_2O$ up to a transpulmonary pressure (Pairway (at opening) or Pplat-Pesophageal measured by an esophageal balloon)<25 cm H2O, with a Pplat<26-32 mm Hg.

Said alpha-2 agonist preferably comprises clonidine or dexmedetomidine.

According to a variant, the method of the invention further comprises, administering a sedative agent S' which is different from an alpha-2 agonist and which does not depress ventilatory drive.

Said sedative agent S' is preferably selected from the group consisting of neuroleptics (e.g.: loxapine, levomepromazine, haloperidol, etc.), hydroxyzine, ketamine, gamma-hydroxybutyric acid and combinations thereof.

Advantageously, sedation and spontaneous ventilation-pressure support-intubation are maintained until the $PaO_2$/$FiO_2$ (P/F) ratio >200 for >12 to 24 h.

According to a particular implementation, the method comprises a step
  d) wherein the trachea of the patient is extubated and a step
  e) wherein sedation and spontaneous ventilation-non invasive ventilation, are maintained until said P/F ratio is >300 for >24 h.

In a preferable way of implementation, sedation and spontaneous ventilation-pressure support of steps a) and c) are maintained with permissive hypercapnia ($PaCO_2$<60 mmHg, arterial blood pH is >7.2).

Advantageously, respiratory rate (RR) may be lowered with mild hypothermia (34-36° C.) so as to obtain a RR compatible with spontaneous ventilation (RR<35-40 breaths per min for a few h; RR<20 bpm for extended periods up to 2-5 days or up to extubation of the patient).

Possibly, the method according to the invention, further comprises:
  f) evaluation of the right ventricular function by daily echocardiography to avoid RV dilatation or septal bulging. Echocardiography should be conducted with incremental PEEP (0-30 cm H2O) to define the tolerance of the RV to high PEEP (8), then combined to passive leg raising to define tolerance to volume loading, in order to lower vasopressor/inotrope requirements.

Possibly, the method according to the invention, further comprises:

g) administering at least one inotrope and/or one vasopressor, as indicated following daily echocardiography.

According to another aspect, the invention pertains to a pharmaceutical composition comprising at least a sedative agent S comprising at least one alpha-2 agonist in combination with at least one sedative agent S' which does not depress ventilatory drive.

Preferably, the alpha-2 agonist sedative agent S comprises clonidine or dexmedetomidine and the sedative agent S' comprises loxapine, or haloperidol.

BRIEF DESCRIPTION OF SEVERAL VIEWS OF THE DRAWINGS

[Not Applicable]

DETAILED DESCRIPTION OF THE INVENTION

Definitions

Abbreviations

| | |
|---|---|
| ALI | acute lung injury (P/F < 300). |
| ARDS | acute respiratory distress syndrome (P/F < 200, absence of increased left atrial pressure). |
| Severe ARDS | P/F < 100 |
| ARF | acute respiratory failure. |
| BiPAP | bi-level positive airway pressure (9) [close to PS]. |
| BIPAP | biphasic intermittent positive airway pressure, biphasic positive airway pressure (10) [close to APRV]. |
| BW | body weight. |
| CCU | critical care unit. |
| CMV | controlled mechanical ventilation. |
| Compliance | volume change per unit of pressure change. |
| d | days |
| driving pressure | Pplat-PEEP. |
| FRC | functional residual capacity. |
| IMV | intermittent mandatory ventilation. |
| LIP | lower inflexion point. |
| LV | left ventricle. |
| MAP | mean arterial pressure. |
| MOF | multiple organ failure. |
| PaO2 | paritial pressure of oxygen in the blood. |
| PaCO2 | partial pressure of the carbon dioxide in the blood. |
| PEEP | positive end-expiratory pressure airway pressure is maintained above atmospheric pressure at the end of expiration by means of a mechanical impedance, usually a valve, within the circuit. The purpose of PEEP is to increase the volume of gas remaining in the lungs (above closing volume) at the end of expiration in order to decrease the shunting of blood through the lungs and improve gas exchange. |
| P/F | PaO2/FiO2 measure of arterial oxygenation efficiency, which corresponds to the ratio of partial pressure of arterial oxygen to the fraction of inspired oxygen |
| PL | transpulmonary pressure - Pairway (at opening) or Pplat-Pesophageal measured by an esophageal balloon. |
| Ppeak | peak pressure. |
| Pplat | plateau pressure measured at end of inspiration. |
| Pflex, Pinf | pressure at lower inflexion point on the incremental limb of pressure-volume curve. |
| PS | pressure support. |
| PSV | pressure support ventilation. |
| P-V | pressure-volume. |
| RR | respiratory rate. |
| RV | right ventricle. |
| SCM | sternocleidomastoid muscle. |
| SV | spontaneous ventilation. |
| SvO2 | mixed venous O2 saturation measured in the pulmonary artery. |
| SsvcO2 | O2 saturation in superior vena cava. |
| transalveolar pressure | Palveolar-Ppleura or Palv-Pinterstitium. |
| UIP | upper inflexion point. |
| Vt | tidal volume. |
| VA/Q | ventilation perfusion ratio. |
| VILI | ventilator-induced lung injury. |
| ZEEP | zero PEEP. |

Preliminary Steps

The trachea of the patient suffering from ARDS is intubated. The lungs are ventilated in a conventional manner (controlled mechanical ventilation: CMV). Following tracheal intubation, the sedation is changed over to an alpha-2 agonist. Then, following return of spontaneous ventilation, CMV is switched over to pressure support (PS) ventilation.

Step a) Sedation:

It consists in continuous administration, without any bolus administration or any rapid infusion, of alpha-2 agonist (initial dosage: dexmedetomidine 0.5-1 µg·kg-1·h-1 or clonidine 1 µg·kg-1·h-1)[1].

[1] To our knowledge, there are no publications showing some equivalence between the 2 drugs. Given the ceiling effect observed with dexmedetomidine 1.5 µg·kg-1·h-1 (11) and the upper dosage for clonidine 2 µg·kg-1·h-1 recommended by the french society of critical care medicine (12), a 1 (dexmedetomidine) to 2 (clonidine) equivalence will be taken for granted in this description. Finally the initial dosage recommended here is tailored to the very patient, according to his neurological response, and to his renal or hepatic pathology.

If, after 3-6 h, sedation is inappropriate (Ramsay (13) scale <2 or patient trying to pull out arterial or central venous catheters or tracheal tube or movement of the patient trying to head out of bed or combative patient) sedation is to be increased to 3<Ramsay<4: dexmedetomidine and clonidine are to be increased to 1.5-2 µg·kg-1·h-1 or 2-4 µg·kg-1·h-1 respectively.

If sedation is still inappropriate, a second sedative agent S' is to be administered which is different from alpha-2 agonist but should not depress ventilatory drive e.g. hydroxyzine 100-200 mg at night time (e.g. 9 PM) or loxapine 100 mg through the nasogastric tube 4 times per day. This dose should be adjusted to 25 mg*4 as early as possible to achieve 3<Ramsay>4). Other sedative agents to be considered are neuroleptics (e.g. haloperidol) (14), ketamine, hydroxyzine, gamma hydroxy butyric acid or other drugs as long as they do not depress ventilatory drive.

Step b) Oxygenation:

Investigators (15) recommend to perform a computerized scanner (CT scan) of the thorax and a pressure-volume (PV) curve (16) before heading into treatment of severe diffuse ARDS. The PV curve allows determination of Pflex on the incremental or decremental limb of the curve. If Pflex cannot be determined, PEEP has to be set to 15-16 cm H2O, according to experienced investigators (17, 18). Given these recommendations, high PEEP is set to 10-24 cm H20.

Step c) CO2 Elimination; Reduced Respiratory Work.

Given spontaneous ventilation, PS ventilation is set to 5-10 cm H2O or to a transpulmonary pressure (Pairway (at opening) or Pplat-Pesophageal measured by an esophageal balloon)<25 cm H2O. An esophageal balloon is to be inserted to determine a transpulmonary pressure<25 cm H20. If an esophageal balloon cannot be inserted, absence of sternal notch retraction, thoraco-abdominal dyscoordination and use of accessory muscles should be assessed e.g. by palpation of the sternocleido mastoid muscle. Then PS is set to a level (usually (~10 cm H2O) so as to suppress sternal notch retraction, thoraco-abdominal dyscoordination and use of accessory muscles (e.g sterno cleido mastoid muscle).

Step d) Curing ARDS:

As the definition of severe ARDS is a P/F<200, steps b and c (oxygenation and reduced respiratory work) are to be maintained up to an increase in P/F>200. If Chest XRay, markers of inflammation (temperature, CRP, PCT, etc.) are improving together with P/F>200, the trachea of the patient is extubated. This process lasts typically 2-5 days using the settings above detailed (PEEP=10-24 cm H20, PS=5-10 cm H20). First Inspired oxygen is to be reduced to F102=0.4 as hypoxia and P/F improved. Then, when F102 is reduced to 0.4, PEEP is reduced every 12 or 24 h from 10-24 cm H2O stepwise by 5 cm H2O to PEEP=5-10 cm H20, as long as P/F keeps increasing toward 200.

Other methods of respiratory assistance may be considered: airway pressure release ventilation, BiPAP, "noisy" PS, intermittent assist control ventilation with very low mandatory rate, neurally adjusted artificial ventilation (NAVA), high frequency ventilation, etc. The core of the process is to combine a sedation without any respiratory depressant effect with a high PEEP and a ventilatory mode as close as possible to spontaneous ventilation to minimize respiratory work and respiratory asynchrony.

Step e) Permissive Hypercapnia:

Given a Pplat<26-32 cm H20, PaCO2 is to be maintained so as to avoid right ventricular failure (19). Usually, PaCO2 and pH are to be <60 mm Hg and >7.2 respectively.

Step g) Mild Hypothermia:

To avoid excessive respiratory work, 2 issues are to be considered:

To avoid re-expansion of alveoli upon each inspiration, the closing volume should be maintained above functional residual capacity residual upon end-expiration.

To avoid excessive respiratory work, respiratory rate (RR) should be maintained as low as possible, especially when oxygen demands are high (7) (e.g. sepsis, etc). While tolerating a RR=35-40 breaths per min (bpmin) is possible for a short period of time (1-3 h) e.g. to allow for compensation of acidosis, a RR<20 bpmin is mandatory for an extended period of time (2-5 days) to observe improvement in P/F. Therefore, sedation should be adequate (3<Ramsay<4: see above). In addition, mild hypothermia (34-36° C.) allows one to lower RR<20 bpmin: surface cooling, hypothermia evoked by the extra renal therapy, if appropriate for the considered patient.

Step f) Improving Circulatory Function:

A key objective is to bring enough blood to the alveoli, reopened by a high PEEP. Echocardiography should performed at least daily to observe right and left ventricular function. Increasing levels of PEEP (0-30 cm H20) (8) are to be used while the RV function is observed qualitatively (dilatation of RV, septal bulging: inverse positioning of the intra ventricular septum due to high pressure in the right ventricle) and quantitatively (TAPSE: tricuspid annular plane systolic excursion). When the best compromise between high PEEP and RV function has been achieved, passive leg rising is to be performed to assess the possibility to increase blood volume and lower the requirements in vasopressors/inotropes. Between echocardiographic assessments, oxygen saturation in the superior vena cava is to be assessed every 6-12 h and maintained >70-75%, as an index of adequacy of cardiac output (20).

Step g) Non-Invasive Ventilation to Deal with Acute Lung Injury (200<P/F<300).

Following extubation, sedation with an alpha-2 agonist should be maintained to observe a quiet cooperative patient (2<Ramsay<3) able to withstand NIV for an extended period of time: usually: 23 h out of 24 h for the first day, then 18 out of 24 h, then 12 out of 24 h, then 6 out of 24 h.

EXAMPLE

Mrs X, 63 years old, 1.55 m, 145 kg, BMI=61, diabetes type 1, oliguric for ≥36 h, associated to mild pulmonary infection, had been bed-ridden with little food intake at home for 3-4 days. She was admitted to the CCU on day 2 (D2) for acute renal failure, acute volume overload. Upon rapid sequence induction-Sellick manoeuver, the patient aspirated. An 8.5 mm tracheal tube was inserted. CMV and sedation (midazolam-sufentanil-cisatracurium) were begun. A fiberoptic bronchoaspiration was performed. On the morning of D3, P/F was 56 (FiO2=1, PEEP=10, Vt=5-6 ml·kg-1, f=20, Drager Evita4). Chest X-ray showed major bilateral infiltrates, predominating on the right side ("white" right lung). On the morning of D3, clonidine was begun (1 µg·kg·h-1, no bolus). After resuming SV, PS (8-12 mm Hg, trigger set to the minimum, 100% automatic tube compensation, Vt=3.5-5.5 ml·kg-1 actual body weight) maintained 40≤PaCO2≤50 mm Hg, pH>7.2, 15<respiratory rate (RR)<25 bpmin, without substernal retraction, use of accessory muscles, nor dyscoordination of thoraco-abdominal muscles. PEEP was set to 15 cm H2O on D3, 20 cm H2O on D4-5-6, 15 cm H2O on D6-7. Peak pressure upon PS remained≤32 mm Hg. As Pplat could not be red upon PS on the ventilator and as PL was not measured, Pplat was equated to peak pressure for simplicity. FiO2 was lowered progressively from 1 to 0.4 on D4-5-6. On D8, given a P/F=262 and cleared chest X-ray, PEEP was reset to 15. Superior vena cava $O_2$ saturation remained>70% at all intervals with dobutamine (D3 to D6) 2 then 1 µg·kg-1·min-1. Repeated echocardiography showed no right ventricular (RV) dilatation, nor septal bulging. CVVHDF combined to forced diuresis (mean arterial pressure>100 mm Hg with noradrenaline [NA] 0.45 µg·kg-1·min-1 lowered to 0.01 µg·kg-1·min-1 and high dose furosemide+edecrine) lowered weight (D3: 150 kg; D7: 143 kg). Under clonidine 1 µg·kg-1·h-1, the Ramsay score progressively lowered (Ramsay 5-6 to 2-3): Mrs X communicated with her family on D5. Sedation was increased with clonidine 2 µg·kg-1·h-1, combined to loxapine 25-100 mg, to Ramsay≥3. On D9, under clonidine 1 µg·kg-1·h-1, the patient was extubated to non-invasive ventilation (NIV: CPAP=10+PS=10) and physiotherapy on D8-9-10-11 and discharged to the floor on D12.

Comments:

This observation show the positive role of alpha-2 agonists in the treatment of severe diffuse ARDS (P/F=56), together with a fine tuning of the ventilator with respect to the considered patient: oxygenation failure per se (high PEEP), as opposed to an absence of respiratory pump failure (spontaneous ventilation-pressure support ventilation). Evidently, treatment of acute renal failure, volume overload and sepsis were contributive to the outcome.

REFERENCES

1. Jardin F. Acute leftward septal shift by lung recruitment maneuver. Intensive Care Med. 2005; 31:1148-9.
2. Papazian L, Forel J M, Gacouin A, Penot-Ragon C, Perrin G, Loundou A, et al. Neuromuscular blockers in early acute respiratory distress syndrome. N Engl J. Med. 2010; 363: 1107-16.
3. Gainnier M, Papazian L. Paralysis during mechanical ventilation in acute respiratory distress syndrom: back to the future ? a reply. Crit Care Med. 2004; 32:1629-30.

4. Wrigge H, Downs J B, Hedenstierna G, Putensen C. Paralysis during mechanical ventilation in acute respiratory distress syndrome: back to the future? Crit Care Med. 2004; 32:1628-9.
5. Putensen C, Zech S, Wrigge H, Zinserling J, Stuber F, von S T, et al. Long-term effects of spontaneous breathing during ventilatory support in patients with acute lung injury. Am J Respir Crit Care Med. 2001; 164:43-9.
6. Chiumello D. Spontaneous breathing during mechanical ventilation. Crit Care Med. 2005; 33:1170-1.
7. Marini J J. Spontaneously regulated vs. controlled ventilation of acute lung injury/acute respiratory distress syndrome. Curr Opinion CritCare. 2011; 17:24-9.
8. Jardin F, Farcot J C, Boisante L, Curien N, Margairaz A, Bourdarias J P. Influence of positive end-expiratory pressure on left ventricular performance. N Engl J. Med. 1981; 304:387-92.
9. Silver M R. BIPAP: useful new modality or confusing acronym? Crit Care Med. 1998; 26:1473-4.
10. Putensen C, Wrigge H. Clinical review: biphasic positive airway pressure and airway pressure release ventilation. Crit Care. 2004; 8:492-7.
11. Venn R M, Newman P J, Grounds R M. A phase II study to evaluate the efficacy of dexmedetomidine for sedation in the medical intensive care unit. Intens Care Med. 2003; 29:201-7.
12. Sauder P, Andreoletti M, Cambonie G, Capellier G, Feissel M, Gall 0, et al. Sedation and analgesia in intensive care. French Critical Care Society. Ann Fr Anesth Reanim. 2008; 27:541-51.
13. Ramsay M A E, Savege T M, Simpson B R J, Goodwin R. Controlled sedation with alphaxolone-alphadolone. Br Med J. 1967; 2:656-9.
14. Shehabi Y, Botha J A, Ernest D, Freebairn R C, Reade M, Roberts B L, et al. Clinical application, the use of dexmedetomidine in intensive care sedation. Crit Care Shock. 2010; 13:40-50.
15. Rouby J J, Lu Q, Goldstein I. Selecting the right level of positive end-expiratory pressure in patients with acute respiratory distress syndrome. Am J Respir Crit Care Med. 2002; 165:1182-6.
16. Lu Q, Vieira S R, Richecoeur J, Puybasset L, Kalfon P, Coriat P, et al. A simple automated method for measuring pressure-volume curves during mechanical ventilation. Am J Respir Crit Care Med. 1999; 159:275-82.
17. Villar J, Kacmarek R M, Perez-Mendez L, guirre-Jaime A. A high positive end-expiratory pressure, low tidal volume ventilatory strategy improves outcome in persistent acute respiratory distress syndrome: a randomized, controlled trial. Crit Care Med. 2006; 34:1311-8.
18. Amato M B, Barbas C S, Medeiros D M, Magaldi R B, Schettino G P, Lorenzi-Filho G, et al. Effect of a protective-ventilation strategy on mortality in the acute respiratory distress syndrome. N Engl J. Med. 1998; 338:347-54.
19. Mekontso D A, Charron C, Devaquet J, Aboab J, Jardin F, Brochard L, et al. Impact of acute hypercapnia and augmented positive end-expiratory pressure on right ventricle function in severe acute respiratory distress syndrome. Intensive Care Med. 2009; 35:1850-8.
20. Marini J J, Gattinoni L. Ventilatory management of acute respiratory distress syndrome: a consensus of two. Crit Care Med. 2004; 32:250-5.

The invention claimed is:

1. A method for treating early severe diffuse acute respiratory distress syndrome (ARDS) in an intubated-ventilated patient, said method comprising the following steps:
a) sedating said patient with a sedating agent S comprising at least one alpha-2 agonist to Ramsay sedation scale: 3<Ramsay<4,
b) applying positive end expiratory pressure PEEP of 10-24 cm H2O;
c) maintaining spontaneous ventilation and applying pressure support ventilation: 5-10 cm $H_2O$ or up to a transpulmonary pressure<25 cm H2O, with a plateau pressure (Pplat)<26-32 mm Hg).

2. The method of claim 1, wherein said alpha-2 agonist comprises clonidine or dexmedetomidine.

3. The method of claim 1, further comprising, administering a sedative agent S' which differs from the sedating agent S and which does not depress ventilatory drive.

4. The method of claim 3, wherein said sedative agent S' is selected from the group consisting of neuroleptics, hydroxyzine, ketamine, gamma-hydroxybutyric acid and combinations thereof.

5. The method of claim 1, wherein sedation and spontaneous ventilation-pressure support-intubation of steps a) and c) are maintained until the $PaO_2/FiO_2$ (P/F) ratio >200 for >12 h to 24 h.

6. The method of claim 1, comprises a step d) wherein the trachea of the patient is extubated and a step e) wherein sedation (2<Ramsay<3) and spontaneous ventilation-non invasive ventilation, are maintained until said P/F ratio is >300 for 24 h.

7. The method of claim 1, wherein sedation and spontaneous ventilation-pressure support of steps a) and c) are maintained with permissive hypercapnia ($PaCO_2$<60 mmHg, arterial blood pH >7.2).

8. The method of claim 1, wherein respiratory rate is controlled with mild hypothermia (34-36° C.) so as to obtain a respiratory rate (RR) compatible with spontaneous ventilation and lowered oxygen demand (RR<35-40 breaths per min for a few h; RR<20 bpm for extended periods: 2-5 days).

9. The method of claim 1, further comprises:
f) evaluation of the right ventricular function by daily echocardiography to avoid RV dilatation or septal bulging, wherein the echocardiography should be conducted with incremental PEEP (0-30 cm H2O) to define the tolerance of the RV to high PEEP and wherein once the best compromise between PEEP and RV function is achieved, passive leg raising will define tolerance to volume loading, to reduce requirements of vasopressor or inotrope.

10. The method of claim 1, further comprises:
g) administering at least one inotrope or vasopressor, as indicated following daily echocardiography.

* * * * *